United States Patent
Staggs

[11] Patent Number: 5,852,794
[45] Date of Patent: Dec. 22, 1998

[54] MULTIPLE FREQUENCY UNAMBIGUOUS PHASE DETECTOR FOR PHACOEMULSIFICATION SYSTEM

[75] Inventor: James W. Staggs, Laguna Niguel, Calif.

[73] Assignee: Allergan, Waco, Tex.

[21] Appl. No.: 787,229

[22] Filed: Jan. 22, 1997

[51] Int. Cl.$^6$ ........................................................ G01R 13/00
[52] U.S. Cl. ............................ 702/72; 310/318; 324/76.49
[58] Field of Search .................................. 364/483, 484, 364/422; 702/72; 310/318, 319; 324/76.39, 76.49

[56] References Cited

U.S. PATENT DOCUMENTS

| | | | |
|---|---|---|---|
| 4,954,960 | 9/1990 | Lo et al. | 364/484 |
| 4,970,656 | 11/1990 | Lo et al. | 364/481 |
| 5,001,649 | 3/1991 | Lo et al. | 364/484 |
| 5,431,664 | 7/1995 | Ureche et al. | 606/128 |

Primary Examiner—Emanuel Todd Voeltz
Assistant Examiner—Matthew Smithers
Attorney, Agent, or Firm—Walter A. Hackler

[57] ABSTRACT

A method for determining the voltage current phase relationship of a piezoelectric phacoemulsification handpiece includes the steps of obtaining an AC voltage signal corresponding to the operating AC voltage of a piezoelectric handpiece and obtaining an AC current signal corresponding to the operating AC current of the piezoelectric handpiece. From said AC current signal, onset of a current cycle is determined and after onset of the current cycle, a voltage ($V_I$) corresponding to a time necessary for the AC current signal to reach a maximum value is produced. Also, after onset of the current cycles, a voltage ($V_v$) corresponding to a time necessary for the AC voltage signal to reach a maximum value is produced. Using an A/D converter, a digital output ($D_v$) corresponding to ($V_v$) is produced and a digital output ($D_I$) corresponding to ($V_I$) is produced. Comparing ($D_v$) and ($D_I$) determines the phase relationship between the voltage and current of the piezoelectric phacoemulsification handpiece.

6 Claims, 2 Drawing Sheets

MULTIPLE FREQUENCY UNAMBIGUOUS PHASE DETECTOR FOR PHACOEMULSIFICATION SYSTEM

The present invention generally relates to the tuning of a piezoelectric phacoemulsification handpiece, more specifically, to a method for determining the phase angle between voltage applied to the piezoelectric transducer and the current drawn by the piezoelectric transducer, and still more particularly, directed to a multiple frequency unambiguous phase detector for phacoemulsification systems.

Phacoemulsification systems typically include a handpiece having an ultrasonically vibrated hollow needle and an electronic control therefor.

As is well known in the art, the phacoemulsification handpiece is interconnected with the control council by an electric cable for powering and controlling the piezoelectric transducer and tubing for providing irrigation fluid to the handpiece and withdrawing aspiration fluid from an eye through the handpiece.

The hollow needle of the handpiece is typically driven or excited along its longitudinal axis by the piezoelectric effect in crystals created by an AC voltage applied thereto. The motion of the driven crystal is amplified by a mechanically resonant system within the handpiece, such that the motion of the needle connected thereto is directly dependent upon the frequency at which the crystal is driven, with a maximum motion occurring at a resonant frequency.

The resonant frequency is dependent, in part upon the mass of the needle interconnected therewith, which is vibrated by the crystal.

For pure capacitive circuits, there is a 90 degree phase angle between a sine wave representing the voltage applied to the handpiece and the resultant current into the handpiece. This is expressed by the angle ø equaling −90 degrees. For a purely inductive circuit, the phase angle ø equals +90 degrees and, of course, for purely resistive circuits ø=zero.

A typical range of frequency used for phacoemulsification handpiece is between about 30 kHz to about 50 kHz. A frequency window exists for each phacoemulsification handpiece that can be characterized by the handpiece impedance and phase.

This frequency window is bounded by an upper frequency and a lower cutoff frequency. The center of this window is typically defined as the point where the handpiece electrical phase reaches a maximum value.

At frequencies outside of this window, the electrical phase of the handpiece is equal to −90 degrees.

Handpiece power transfer efficiency is given by the formula (V*I)(COSø). This means that the most efficient handpiece operating point occurs when the phase is closest to ø degrees.

In order to maintain optimum handpiece power transfer efficiency, it is important to control the frequency to achieve a phase value as close to zero degrees as possible.

This goal is complicated by the fact that the phase angle of the ultrasonic handpiece is also dependent on the loading of the transducer which occurs through the mechanically resonant system which includes the needle.

That is, contact with the needle with tissue and fluids within the eye create a load on the piezoelectric crystals with concomitant change in the operating phase angle.

Consequently, it is important to determine and measure the phase angles at all times during operation of the handpiece in order to adjust the driving circuitry to achieve an optimum phase angle in order to effect constant energy transfer into the tissue by the phaco handpiece, regardless of loading effects.

Thus, it is important to provide automatic tuning of the handpiece during its use in phacoemulsification tissue and withdrawing same from an eye. This auto tuning is accomplished by monitoring the handpiece electrical signals and adjusting the frequency to maintain consistency with selected parameters.

In any event, control circuitry for phacoemulsification handpiece can include circuitry for measuring the phase between the voltage and the current, typically identified as a phase detector. However, problems arise in the measurement of the phase shift without dependence on the operating frequency of the phacoemulsification handpiece. That is, because, as hereinabove noted, the phase shift is dependent on the operating frequency of the handpiece and air and time delay in the measurement thereof requires complex calibration circuitry in order to compensate to provide for responsive tuning of the handpiece.

Phase detection is the process of applying two electrical periodic signals of similar frequency into an electrical circuit that generates a voltage proportional to the time (phase) difference between the two signals.

This voltage generated by the phase detector is then usually time averaged either by an electronic circuit or sampled by an A/D converter and then averaged digitally.

The averaged signal can be read by a conventional voltage meter or used by a microprocessor as data for processing. The averaging also helps to reject electrical noise.

As was described earlier, the output of a phase detector is proportional to the difference in time (of occurrence) of two signals. By definition, this means that while the electrical output of a conventional phase detector is a function of the signal phase, it is also directly proportional to the frequency of use. This means that the frequency of use must be known and compensated for when reading the phase detector output in order to derive quantified phase values. While, as hereinabove noted, a calibration circuit can account for the variation of the frequency, such a circuit is usually very complex and may require the use of a microcontroller. In addition, neither of these approaches account for the drift in performance over time which is typical of phacoemulsification handpieces.

This problem was recognized in U.S. Pat. No. 5,431,664, which provided a solution by using the admittance of the transducers as the tuning parameter rather than the phase-angle. The necessary circuitry is, of course, complicated and accordingly there is still a continuing need for a method for determining real time electrical phase for a piezoelectric phacoemulsification handpiece which is consistent over the entire handpiece range of operation which does not require further calibration circuitry for the controller.

SUMMARY OF THE INVENTION

In accordance with the present invention, a method for determining the voltage current phase relationship of a piezoelectric phacoemulsification handpiece generally includes the steps of obtaining an AC voltage signal corresponding to the operating AC voltage of a piezoelectric handpiece along with an AC current signal corresponding to the operating AC current of the piezoelectric handpiece.

From the AC voltage signal, onset of voltage cycle is obtained. More particularly, the onset may be determined when the AC voltage increases while crossing a value of zero volts.

From the AC current signal, onset of a current cycle is obtained. More particularly, the onset may be determined when the AC current increases while crossing a zero current value.

After onset of the current cycle, a voltage ($V_1$) corresponding to a time necessary for the AC current signal to reach a maximum value is produced. In addition, after onset of the current cycle, a voltage ($V_v$) corresponding to a time necessary for the AC voltage signal to reach a maximum value as produced.

Once the signals corresponding to handpiece voltage and handpiece current have been obtained and converted to logic levels, they are then used for processing.

A reference clock is taken that is equal to the handpiece clock frequency divided by two. This signal is fed into an integrator that converts the period of one clock cycle to a voltage. This voltage is inversely proportional to frequency.

The voltage logic signal and current logic signals are supplied to a circuit that generates a pulse that is proportional to the phase difference between the two signals.

The designation of the two circuits previously described are V (reference) and V (phase). V (reference) is provided to the voltage reference of an A/D converter. The resulting output of the A/D converter is a digital value that is proportional to the actual handpiece phase in degrees that is not dependent on the frequency.

BRIEF DESCRIPTION OF THE DRAWINGS

The advantages and the features of the present invention will be better understood by the following detailed description when considered in conjunction with the accompanying drawings, in which.

DETAILED DESCRIPTION

Figure 1:
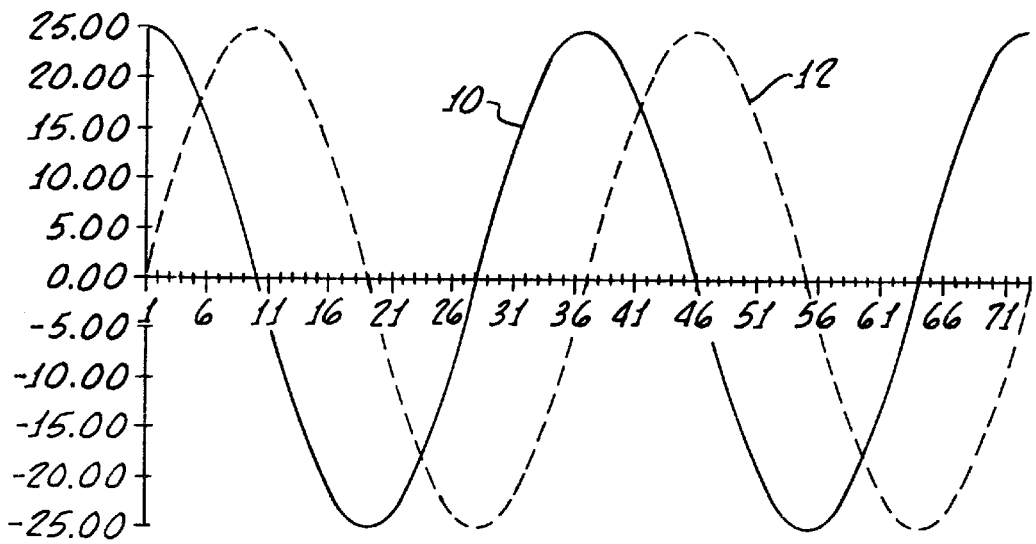
FIG. 1 is a plot of the 90 degree phase shift between the sine wave representation of the voltage applied to a piezoelectric phacoemulsification handpiece and the resultant current into the handpiece.

The typical range of frequencies used for phacoemulsification handpieces is between about 30 kHz and about 50 kHz. When the frequency applied to the handpiece is significantly higher, or lower than resonancy, it responds electrically as a capacitor. The representation of this dynamic state is shown in FIG. 1 in which curve 10 (solid line) represents a sine wave corresponding to handpiece current and curve 12 (broken line) represents a sine wave corresponding to handpiece voltage.

Figure 2:
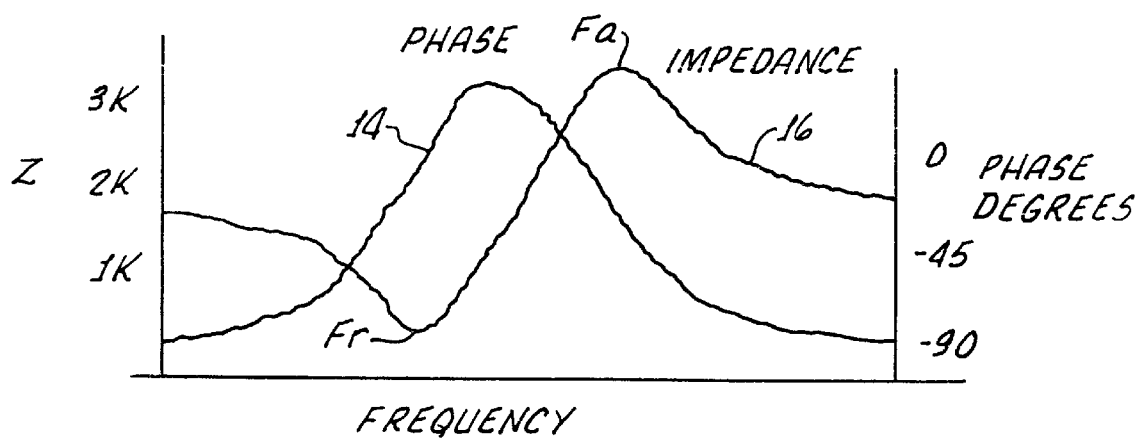
FIG. 2 is a plot of the phase relationship and the impedance of a typical piezoelectric phacoemulsification handpiece.

The impedance of the typical phacoemulsification handpiece varies with frequency, i.e., it is reactive. The dependence of typical handpiece phase and impedance as a function of frequency is shown in FIG. 2 in which curve 14 represents the phase difference between current and voltage of the handpiece as function frequency and curve 16 shows the change in impedance of the handpiece as a function of frequency. The impedance exhibits a low at "Fr" and a high "Fa" for a typical range of frequencies.

Automatic tuning of the handpiece, as hereinabove briefly noted, is typically accomplished by monitoring the handpiece electrical signals and adjusting the frequency to maintain a consistency with selected parameters.

In order to compensate for a load occurring at the tip of the phacoemulsification handpiece, the drive voltage to the handpiece can be increased while the load is detected and then decreased when the load is removed. This phase detector is typically part of the controller in this type of system.

In such conventional phase detectors, the typical output is a voltage as proportional to the difference in alignment of the voltage and the current waveform, for example, −90 degrees as shown in FIG. 1. As shown in FIG. 2, it is important to consider that during the use of the handpiece, the waveform is of varying in phase and correspondingly the output waveform is also varying.

Heretofore, the standard technique for measuring electrical phase has been to read a voltage that is proportional to phase and also to frequency. This type of circuit can be calibrated for use with a single frequency as changing the frequency would cause the calibration data to be incorrect.

This can also be seen with single frequency systems. The corrected phase value will drift due to variation in the circuit parameters.

The other typical approach is to utilize a microprocessor to compare the value of the phase detector output with that of a frequency detector and compute the true phase. This approach is fairly complex and is subject to drift of the individual circuits as well as resolution limitations.

Figure 3:
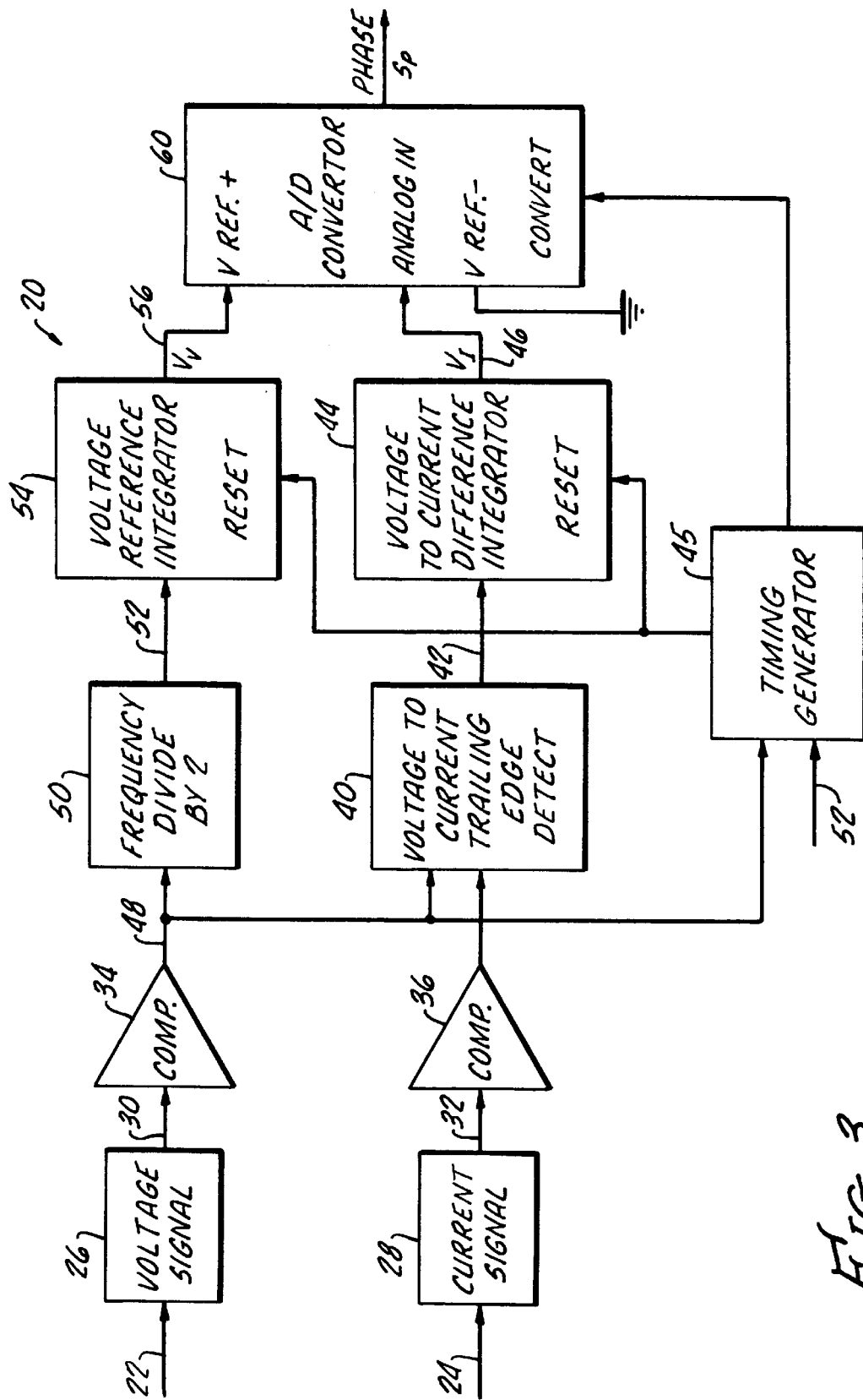
FIG. 3 is a block diagram of improved phase detector circuitry suitable for performing a method in accordance with the present invention.

A block diagram 20 as shown in FIG. 3 is representative of an improved phase detector suitable for performing the method in accordance with the present invention. Each of the function blocks shown comprises conventional state of the art circuitry of typical design and components for producing the function represented by each block as hereinafter described.

The voltage input 22 and current 24 from a phacoemulsification handpiece (not shown) is converted to an appropriate signal using an attenuator 26 on the voltage signal to the phacoemulsification handpiece, and a current sense resistor 28 and fixed gain amplifier for the handpiece current.

Thereafter, an AC voltage signal 30 and AC current signal 32 is passed to comparators 34, 36 which convert the analog representations of the phacoemulsification voltage and current to logic level clock signals.

The output from the comparator 34 is fed into a D flip flop integrated circuit 50 configured as a frequency divide by 2. The output 52 of the integrated circuit 50 is fed into an operational amplifier configured as an integrator 54. The output 56 of the integrator 54 is a sawtooth waveform of which the final amplitude is inversely proportional to the handpiece frequency. A timing generator 45 uses a clock synchronous with the voltage signal to generate A/D converter timing, as well as timing to reset the integrators at the end of each cycle.

This signal is fed into the voltage reference of an A/D converter via line 56.

The voltage leading edge to current trailing edge detector 40 uses a D flip flop integrated circuit in order to isolate the leading edge of the handpiece voltage signal. This signal is used as the initiation signal to start the timing process between the handpiece voltage and handpiece current.

The output 42 of the leading detector 40 is a pulse that is proportional to the time difference in occurrence of the leading edge of the handpiece voltage waveform and the falling edge of the handpiece current waveform.

Another integrator circuit 44 is used for the handpiece phase signal 42 taken from the detector 40 The output 46 of the integrator circuit 44 is a sawtooth waveform in which the peak amplitude is proportional to the time difference in the onset of leading edge of the phacoemulsification voltage and the trailing edge of the onset of the handpiece current waveform. The output 46 of the integrator circuit 44 is fed into the analog input or an A/D (analog to digital converter) integrated circuit 60.

A positive reference input 56 to the A/D converter 60 is a voltage that is inversely proportional to the frequency of operation. The phase voltage signal 46 is proportional to the phase difference between the leading edge of the voltage onset, and the trailing edge of the current onset, as well as inversely proportional to the frequency of operation. In this configuration the two signals Frequency voltage reference 56 and phase voltage 46 track each other over the range of frequencies, so that the output of the A/D converter 60 produces a phase independent of the frequency of operation.

The advantage of utilizing this approach is that the system controller (not shown) is provided with a real time digital phase signal Sp in which 0 to 255 counts will consistently represent 0 to 359 degrees of phase.

The significant advantage is that no form of calibration is necessary since the measurements are consistent despite the frequencies utilized.

For example, using AMPs operation frequencies of 38 kHz and 47 kHz and integrator having a rise time of $150 \times 10^5$ V/sec and an 8 bit A/D converter having 256 counts, a constant ratio is maintained and variation in frequency does not affect the results. This shown in the following examples.

EXAMPLE I

38 KHz Operation

Period of 1 clock cycle=1/F@38 KHz=$26.32 \times 10^{-6}$ S

Portion of one period for I=90 degrees=$26.32 \times 10^{-6}$ S/4= $6.59 \times 10^{-6}$ S Integrator output for one reference cycle=$(150 \times 10^3 V/S) \times (26.32 \times 10^{-6} S)$=3.95 Volts Intearator output from 90 degree cycle duration=$(150 \times 10^3 V/S) \times (6.59 \times 10^{-6} S)$=0.988 Volts Resulting Numerical count from A/D converter=3.95 Volts/256 counts=0.0154 Volts per count Actual Number of A/D counts for 90 degrees at 38 KHz

EXAMPLE 2

47 KHz Operation

Period of 1 clock cycle=1/F@ 47 KHz=$21.28 \times 10^{-6}$ S
Portion of one period for I=90 degrees=$21.28 \times 10^{-6}$ S/4= $5.32 \times 10^{-6}$ S Intearator output for one reference cycle=$(150 \times 10^3 V/S) \times (21.28 \times 10^{-6} S)$=3.19 volts Intearator output from 90 degree cycle duration=$(150 \times 10^3 V/S) \times (5.32 \times 10^{-6} S)$=0.798 Volts Resulting Numerical count from A/D converter=3.19 Volts/256 counts=0.0124 Volts per count Actual Number of A/D counts for 90 degrees at 47 KHz=0.798/0.0124=64 counts Although there has been hereinabove described a method for determining the voltage current phase relationship of a piezoelectric phacoemulsification handpiece in accordance with the present invention, for the purpose of illustrating the manner in which the invention may be used to advantage, it should be appreciated that the invention is not limited thereto. Accordingly, any and all modifications, variations, or equivalent arrangements which may occur to those skilled in the art, should be considered to be within the scope of the present invention as defined in the appended claims.

What is claimed is:

1. A method for determining the voltage-current phase relationship of a piezoelectric phacoemulsification handpiece, said method comprising the steps of:

obtaining an AC voltage signal corresponding to the operating AC voltage of a piezoelectric handpiece;

obtaining an AC current signal corresponding to the operating AC current of the piezoelectric handpiece;

from said AC current signal, determining onset of a current cycle;

after onset of the current cycle, producing a voltage ($V_I$) corresponding to a time necessary for the AC current signal to reach a maximum value;

after onset of the current cycle, producing a voltage ($V_v$) corresponding to a time necessary for the AC voltage signal to reach a maximum value; and using an A/D converter, to produce a digital output signal, ($S_p$), by comparing ($V_v$) to ($V_I$), and determining the phase relationship between the voltage and current of the piezoelectric phacoemulsification handpiece, said phase signal ($S_p$) being frequency independent.

2. The method according to claim 1 wherein the step of determining current cycle onset comprises determining when the AC current increases while crossing a zero current value.

3. The method according to claim 2 further comprising the step of producing a current onset signal and feeding same into the A/D converter.

4. The method according to claim 3 further including the step of providing an integration for producing the ($V_v$) and ($V_I$) voltage and feeding same into the A/D converter.

5. The method according to claim 4 further comprising the step of dividing the AC voltage signal by two, producing a divided voltage signal and feeding same along with the AC voltage signal into the integrator.

6. Apparatus for determining the voltage current phase relationship of a piezoelectric phacoemulsification handpiece, said method comprising the steps of:

means for obtaining an AC voltage signal corresponding to the operating AC voltage of a piezoelectric handpiece;

means for obtaining an AC current signal corresponding to the operating AC current of the piezoelectric handpiece;

means for determining onset of a current cycle from said AC current signal;

means for producing a voltage ($V_I$) corresponding to a time necessary for the AC current signal to reach a maximum value after onset of the current cycle;

means for producing a voltage ($V_v$) corresponding to a time necessary for the AC voltage signal to reach a maximum value after onset of the current cycle; and A/D converter means for comparing ($V_v$) and ($V_I$) to determine the phase relationship between the voltage and current of the piezoelectric phacoemulsification handpiece and generating a phase signal ($S_p$) corresponding thereto, said phase signal being frequency independent.

* * * * *

UNITED STATES PATENT AND TRADEMARK OFFICE
CERTIFICATE OF CORRECTION

PATENT NO. : 5,852,794
DATED : December 22, 1998
INVENTOR(S) : James W. Staggs

It is certified that error appears in the above-identified patent and that said Letters Patent is hereby corrected as shown below:

In column 2, line 2, after "phacoemulsification" and before "tissue" insert --of--.
In column 3, line 57, before "frequency" insert --of--.
In column 4, line 66, after "detector 40" insert --.--
In column 4, line 66, after "detector" insert --.--.
In column 5, line 13, delete "Frequency" and insert therefor --, frequency--.
In column 5, line 16, after "phase" insert --signal $S_p$ --.
In column 5, lines 41, 54 and 56 of the Patent, delete the word "Intearator", each occurrence, and insert therefor --Integrator--.
In column 6, lines 22 through 24, cancel in Claim 1
"using an A/D converter, to produce a digital output signal
($S_p$),
by comparing ($V_v$) to ($V_i$), and determining the phase"
and substitute therefor
--using an A/D converter, to produce a digital output signal
($S_p$), by comparing ($V_v$) to ($V_i$), and determining the phase--.

In column 6, line 44, delete in Claim 6 "method comprising the steps of" and insert therefor --apparatus comprising--.

Signed and Sealed this

Fifteenth Day of June, 1999

Attest:

Q. TODD DICKINSON

*Attesting Officer*  *Acting Commissioner of Patents and Trademarks*